United States Patent
Takahashi et al.

(10) Patent No.: US 7,341,777 B2
(45) Date of Patent: Mar. 11, 2008

(54) COATING FOR INSPECTION OF CRACKING IN STRUCTURE

(75) Inventors: Ichihiko Takahashi, Tokyo (JP); Michio Ushijima, Tokyo (JP); Mitsuhiko Uchida, Tokyo (JP); Tomio Onoguchi, Tokyo (JP)

(73) Assignees: National Maritime Research Institute, Tokyo (JP); Three Bond Co., Ltd., Tokyo (JP)

( * ) Notice: Subject to any disclaimer, the term of this patent is extended or adjusted under 35 U.S.C. 154(b) by 0 days.

(21) Appl. No.: 10/562,505

(22) PCT Filed: Jun. 24, 2004

(86) PCT No.: PCT/JP2004/009266

§ 371 (c)(1),
(2), (4) Date: Dec. 22, 2005

(87) PCT Pub. No.: WO2005/001454

PCT Pub. Date: Jan. 6, 2005

(65) Prior Publication Data

US 2006/0154046 A1    Jul. 13, 2006

(30) Foreign Application Priority Data

Jun. 26, 2003  (JP)  ............................. 2003-181953
Mar. 1, 2004   (JP)  ............................. 2004-055833

(51) Int. Cl.
*B32B 5/16* (2006.01)
(52) U.S. Cl. .................................... 428/323; 428/402.2
(58) Field of Classification Search ..................... None
See application file for complete search history.

(56) References Cited

U.S. PATENT DOCUMENTS

| 3,803,485 | A | * | 4/1974 | Crites et al. | ................. 324/693 |
| 4,624,709 | A | * | 11/1986 | Otsuka | ..................... 106/31.28 |
| 5,534,289 | A | * | 7/1996 | Bilder et al. | .................... 427/8 |
| 2002/0000128 | A1 | | 1/2002 | Williams | |

FOREIGN PATENT DOCUMENTS

| JP | 59-193966 | 11/1984 |
| JP | 1-170672 | 7/1989 |
| JP | 10-267866 | 10/1998 |
| WO | 01/29566 | 4/2001 |

* cited by examiner

*Primary Examiner*—Sheeba Ahmed
(74) *Attorney, Agent, or Firm*—Dilworth & Barrese, LLP

(57) ABSTRACT

In a coating for the inspection of a crack in a structure wherein a coating layer having dispersed therein microcapsules with a visualizing liquid sealed therein is formed on the surface of the structure and when a crack is developed in the structure and propagated to the coating layer, the microcapsules dispersed in the coating layer are ruptured and the visualizing liquid flows out from the ruptured microcapsules and reaches the surface of the coating layer along the crack in the coating layer, thereby making it possible to detect the occurrence of the crack in the structure: at least one second coating layer not containing the microcapsules is formed over the first coating layer with the microcapsules dispersed therein, the second coating layer being transparent and having an outermost layer flexible enough to be prevented from being cracked even upon cracking in the first coating layer.

18 Claims, 1 Drawing Sheet

COATING FOR INSPECTION OF CRACKING IN STRUCTURE

FIELD OF ART

The present invention relates to a coating for the inspection of cracks in structures and more particularly to a coating for the inspection of fatigue cracks in various structures, including ships, bridges, vehicles, aircraft and machine tools.

BACKGROUND ART

Such structures as ships, bridges, vehicles, aircraft and machine tools are constructed mainly of metals such as iron, aluminum and magnesium, and alloys thereof. If a repeated load is imposed on any of these metallic structures, a crack may be developed particularly in a stress-concentrated portion of the metallic structure due to metal fatigue. Since such a fatigue crack of the structure develops gradually with the lapse of time, the structure is inspected for cracks periodically or non-periodically.

Such a crack inspection is generally performed by visual inspection. In a special case, a precise inspection is performed using a device such as, for example, an ultrasonic flaw detector. For example, in JP 4-169836A is disclosed a method wherein a strain varying range of a structure to be inspected is determined from the time when a fine line breaks, thereby accurately predicting the time when a fatigue damage occurred. In JU 1-180757A is disclosed a method wherein a ribbon-like conductive film is formed in a crack detecting portion of a structure, a conduction detector is connected to both ends of the ribbon-like conductive film and fracture of the conductive film simultaneous with cracking of the film is detected by the conduction detector, thereby detecting the occurrence of a fatigue crack in an early stage.

However, all of the above precise inspection methods require the installation of measuring devices and thus cost high. Besides, skill is needed because the handling of measuring devices is troublesome. Further, in case of inspecting a narrow place or a place where various members are installed in a complicated state, it is difficult or impossible to use the measuring devices.

In an effort to solve such problems involved in the inspection methods using measuring devices, an inspection method is disclosed in JP 10-267866A (prior art 1) wherein a coating layer having dispersed therein glass capsules with a visualizing liquid sealed therein is formed on the surface of a structure to be inspected and consequently a crack is developed in the coating layer along a crack developed in the structure, whereby there occurs breakage of the glass capsules in the coating layer and the visualizing liquid flows out onto the surface of the coating layer, thus permitting detection of the cracked portion.

In U.S. Pat. No. 5,534,289 (prior art 2) is disclosed an inspection method wherein a first coating layer having dispersed therein microcapsules with a visualizing liquid sealed therein is formed on the surface of a structure and a second coating layer different in color from the visualizing liquid is formed on the first coating layer, allowing a crack if occurred in the structure to be propagated to the first and second coating layers, resulting in rupture of the microcapsules, then the visualizing liquid flows out from the microcapsules, further flows along the cracks and is sensed upon arrival at the surface of the second coating layer, thereby detecting the occurrence of the crack in the structure. A red dye is used therein as the visualizing liquid.

In the methods disclosed in the prior arts 1 and 2, each using a visualizing liquid, the visualizing liquid oozes out to the surface of a coating layer along a crack developed in a structure and the presence of the crack is checked by seeing the visualizing liquid. However, there has been the problem that the visualizing liquid which has oozed out to the coating layer surface fades little by little with the lapse of time and gradually becomes invisible.

Moreover, in the prior art 2, a red dye of an azo or anthraquinone compound is microencapsulated and is mainly used as a visualizing liquid, and a coating layer with the microcapsules dispersed therein is applied to the surface of a structure. However, in case of using this visualizing liquid, the red visualizing liquid which had appeared with the occurrence of a crack in the structure fades little by little under the influence of ultraviolet light for example and gradually becomes invisible.

OBJECT OF THE INVENTION

The present invention has been accomplished for solving the above-mentioned problems. From the standpoint that the required crack inspection accuracy (visibility based on oozing-out of a dye) is preferably an inspection accuracy to such an extent as does not overlook a crack of a size which is likely to cause an accident before the next inspection, it is an object of the present invention to provide a coating for the inspection of a crack in a structure which coating permits the inspection of a crack in a simple manner even without the use of such a measuring device as in the prior art and provide a coating for the inspection of a crack in a structure which coating can ensure of a long-term of a visualizing liquid which oozes out from broken microcapsules in response to a crack developed in the structure.

DISCLOSURE OF THE INVENTION

The present invention firstly resides in a coating for the inspection of a crack in a structure wherein a coating layer having dispersed therein microcapsules with a visualizing liquid sealed therein is formed on the surface of the structure and when a crack is developed in the structure and propagated to the coating layer, the microcapsules dispersed in the coating layer are ruptured and the visualizing liquid flows out from the ruptured microcapsules and reaches the surface of the coating layer along the crack in the coating layer, thereby making it possible to detect the occurrence of the crack in the structure, characterized in that at least one second coating layer not containing the microcapsules is formed over the first coating layer with the microcapsules dispersed therein, the second coating layer being transparent and having an outermost layer flexible enough to be prevented from being cracked even upon cracking in the first coating layer.

The present invention secondly resides in the above coating for the inspection of a crack in a structure wherein the amount of elongation of the outermost layer is seventeen times or more as large as the amount of elongation of any other layer if present than the outermost layer in the second coating layer.

The present invention thirdly resides in the above coating for the inspection of a crack in a structure wherein the visualizing liquid sealed in the microcapsule contains as principal components a nigrosine compound and a solvent in a weight ratio of the nigrosine compound to the solvent in the range of 1:55 to 1:0.37.

MODE FOR CARRYING OUT THE INVENTION

As the first coating layer as a constituent of the structure crack inspection coating of the present invention there basically may be used a conventional known coating layer containing microcapsules. In this case, as the visualizing liquid to be sealed into the microcapsules there may be used a liquid with a conventional known dye or pigment dissolved or dispersed therein. As example of the dye are mentioned azo and anthraquinone dyes. It is preferable that these dyes be each dissolved in a conventional known hydrophobic solvent such as, for example, mineral oil, oleic acid or linolic acid and be microencapsulated in this liquid state.

The mixing ratio of the dye to the solvent is not specially limited, but from the standpoint of color density and solubility, a dye to solvent mixing ratio in the range of 0.5:9.5 to 2.5:7.5 (weight ratio) is preferred. The visualizing liquid may incorporate a fluorescent dye. In this case, for example when a structure is built in a dark environment within a ship, the fluorescent dye flowing out from the coating layer as a result of formation of a crack can be sharply defined by the radiation of black light, whereby the detection of the crack becomes still easier.

Having made studies also about a visualizing liquid capable of displaying the effect of the present invention to the utmost degree, the present inventors found that a visualizing liquid containing as principal components a nigrosine compound and a solvent in a weight ratio of the nigrosine compound to the solvent in the range of 1:55 to 1:0.37 exhibited a more outstanding effect. The nigrosine compound is nigrosine or a derivative thereof, examples of which include Solvent Black 5 and Solvent Black 7, provided no limitation is made thereto. Also as to the solvent to be used in this case, the foregoing hydrophobic solvent is preferred from the standpoint that it does not dissolve in water such as rain water or sea water upon cracking and development of color.

In the mixing ratio of the nigrosine compound to the solvent, if the solvent is used in a proportion exceeding 55 parts by weight relative to one part by weight of the nigrosine compound, there is not obtained sufficient visibility. If the amount of the solvent used is set smaller than 0.37 part by weight, the viscosity of the visualizing liquid becomes high and it becomes difficult to effect microencapsulation; besides, even if the visualizing liquid is microencapsulated, the amount of the visualizing liquid reaching the surface along a crack becomes smaller.

The thickness of the first coating layer is not specially limited. An optimum thickness range thereof differs depending on the diameter of microcapsule, but is usually 50 to 500 μm, preferably 100 to 350 μm. If the thickness of the first coating layer is smaller than 50 μm, it is required to use microcapsules smaller in average diameter, with the result that the absolute quantity of the visualizing liquid in each capsule becomes short or the capsule becomes difficult to be ruptured, thus leading to deterioration of the color developability. If the thickness of the first coating layer exceeds 500 μm, a crack developed in a structure becomes difficult to be propagated to the coating of the first coating layer.

The diameter of each microcapsule used in the present invention is not specially limited, but it is preferable for the microcapsules to have an average diameter of 30 to 300 μm, more preferably 50 to 200 μm. If the average diameter of the microcapsules is smaller than 30 μm, the absolute quantity of the visualizing liquid in each capsule becomes short or it becomes difficult for the capsule to be ruptured, thus leading to deterioration of color developability. If the average diameter of the microcapsules exceeds 500 μm, a crack developed in a structure becomes difficult to be propagated to the coating of the first coating layer.

In the present invention, the microcapsules containing the visualizing liquid are dispersed to form the first coating layer. As the material which forms the coating layer, any of various curable or solidifying resin compositions used in coating materials or coating agents is employable preferably. As examples of such resin compositions there are mentioned epoxy-, urethane-, acryl-, nitrocellulose-, silicone- and modified silicone-based coating materials and coating agents. Particularly, epoxy resins such as bisphenol A and bisphenol F are preferred. These coating materials and coating agents may contain as a principal component a reactive resin composition which cures for example on heating or upon exposure to moisture or light or by two-liquid mixing. Alternatively, there may be adopted a method wherein each of the above various resins is dissolved in a solvent, then is applied in this state to an object to be coated and is solidified by evaporation of the solvent. Further, both methods may be used in combination.

For shielding the surface color of the microcapsules containing the visualizing liquid and of the structure to be coated and for ensuring visibility based on efflux of the visualizing liquid, it is preferable that a binder which forms the first coating layer be opaque. Particularly, it is preferred that the binder be colored in white color such as white or milky white. As examples of materials employable effectively for such coloration there are mentioned white pigments and fillers, including titanium oxide, calcium carbide and talc.

As a method for producing the microcapsules containing the visualizing liquid there may be adopted a conventional known method such as, for example, coacervation method, in-situ polymerization method, interfacial polymerization method, or submerged curing method. As the material of the microcapsules, gelatin is suitable taking into account the stability of the microcapsule film when forming a coating layer on the surface of an object to be coated.

The blending ratio of the binder component to the visualizing liquid-containing microcapsules, both forming the first coating layer, depends on the amount of the visualizing liquid contained in each microcapsule and the microcapsule diameter, but is approximately 4:1 as a resin to microcapsule weight ratio or approximately 2.5:1 as a resin to microcapsule volume ratio. The lower the proportion of microcapsules than the above reference value, the less satisfactory becomes the development of color upon occurrence of a crack. The higher the said proportion, the easier the occurrence of rupture of microcapsules when forming a coating or the higher the viscosity of the coating material, which makes the application of the coating material difficult.

In the present invention, the second coating layer is applied over the first coating layer thus formed. It is optional whether the second coating layer is to be constituted by only an outermost layer or should have one or more other layers (hereinafter referred to as the "intermediate layer") than the outermost layer. As the intermediate layer, an opaquely colored layer is preferred. With the intermediate layer, it is possible to improve the appearance characteristic of the first coating layer and thereby improve the visibility when color is developed. The thickness of the intermediate layer is not specially limited, but is preferably 50 to 500 μm, more preferably 100 to 350 μm. If the thickness of the intermediate layer is smaller than 50 μm, it is difficult for the intermediate layer to fulfill its function to a satisfactory extent, and if it exceeds 500 μm, a crack developed in a structure becomes difficult to be propagated to the coating layer.

As the material (coating material) which forms the opaquely colored intermediate layer there may be used, as is the case with the first coating layer, any of various liquid compositions containing, for example, epoxy resin, urethane resin, acrylic resin, silicone resin, or modified silicone resin, as a principal component. Among them, reactive resin compositions are preferred, taking environmental pollution and working environment into account. Particularly, the same type of resin as that used in the first coating layer is preferred, with epoxy resin being most preferred. The object of the present invention can be achieved by adopting the two-layer structure comprising the first coating layer having dispersed therein microcapsules containing the visualizing liquid and the second coating layer not containing microcapsules and having a transparent outermost layer. Thus, the second coating layer is not always required to have plural layers, but in the case where the second coating layer has plural layers, it is preferable that the outermost layer be a transparent layer and the other intermediate layer(s) be a layer(s) functioning to hold within the layer(s) the visualizing liquid flowing out due to the occurrence of a crack and thereby maintain the development of color. In this sense, it is preferable for the intermediate layer(s) be a layer having such a color as white or milky white. The intermediate layer(s) also functions as a protective layer for preventing the microcapsules in the first coating layer from being broken by an external shock such as a flying stone. Further, with the two-layer structure comprising the first coating layer with microcapsules dispersed therein and the transparent second coating layer, it is impossible to completely shield the color of the visualizing liquid and therefore the color contrast in color development tends to be weak.

The transparent outermost layer forming the whole or part of the second coating layer is required to have flexibility to prevent a crack from being developed following a crack of a structure. As a guideline of this flexibility it is necessary that the elongation of the layer (coating) be large although it is also influenced by the adhesion between the transparent outermost layer and the other layer (the first coating layer or the intermediate layer in the second coating layer) laminated thereto. Preferably, the amount of elongation of the outermost layer is seventeen times or more as large as the elongation of the other coating layers. On the other hand, if the amount of elongation of the outermost layer is smaller than about five times that of the other coating layers, the outermost layer will be cracked almost simultaneously with the occurrence of a crack in any other layer and the visualizing liquid will flow out from the crack, so that it become difficult to ensure visibility over a long period when the crack inspection coating is used in water or sea water or when it is applied to a portion exposed to rain water. It is preferable that the first coating layer containing microcapsules be high in adhesion to a structural base and low in elongation. The elongation of the first coating layer be preferably not larger than 3 mm, more preferably not larger than 1 mm.

It is preferable for the outermost layer in the second coating layer to have an adhesive strength under shear between it and the immediately underlying coating layer of not higher than 1 MPa. If the outermost layer is in close contact with the immediately underlying layer under a high adhesive strength, it is easily influenced and cracked by displacement of the structure and the immediately underlying layer. On the other hand, if the adhesive strength is low, a gap is apt to be formed between the outermost layer and the immediately underlying coating layer and the outermost layer becomes difficult to be influenced by the displacement. As the material of the outermost layer in the second coating layer, a suitable material which satisfies the foregoing flexibility is selected from among, for example, solvent-diluted type rubbery coating materials such as polyisobutylene rubber and styrene-butylene copolymer rubber and various fluid compositions containing as principal components epoxy resin, urethane resin, acrylic resin, silicone resin and modified silicone resin.

The thickness of the outermost layer is usually in the range of 10 to 500 μm, preferably 20 to 200 μm. If it is smaller than 10 μm, there arises a fear that a crack propagated to the first coating layer and further to the intermediate layer may be formed also in the outermost layer. If it exceeds 500 μm, a bad appearance is apt to occur.

It is necessary that the outermost layer be transparent. However, by the term "transparent" as referred to herein, it is meant that the outermost layer be transparent to such an extent as the state of at least the immediately underlying layer is visible. The outermost layer may be colored insofar as it retains transparency, but it is most preferred that the outermost layer be colorless and transparent. It is preferable that the transparency be not lower than 50% in terms of a percent light transmission in the visible light region.

As a combination of preferred materials of the first coating layer, an optional intermediate layer and the transparent outermost layer, mention may be made of a combination of epoxy resin (first coating layer), epoxy resin (intermediate layer) and polyisobutylene rubber (transparent outermost layer).

Next, the following description is provided about a process for applying the crack inspection coating of the present invention to a structure. First, a coating composition is prepared by mixing microcapsules containing a visualizing liquid with a resin composition which forms a first coating layer. Then, this liquid composition is applied with a brush or the like to the surface of a structure to be inspected for a crack. How to apply the liquid composition to the structure to be inspected is not specially limited insofar as the coating method adopted does not cause breakage of the incorporated microcapsules.

Next, a resin composition for forming a second coating layer is prepared in advance and is applied over the first coating layer formed as above to form a second coating layer. In this case, this second coating layer, as well as the first coating layer, may be formed by a conventional known method such as, for example, brush coating, roll coating, or spray coating. In case of forming plural second layers, the coating operating may be repeated using the above method.

In to the resin composition serving as the binder for forming the first and second coating layers in the present invention there may be incorporated conventional known additives as necessary insofar as the performance inherent in the resin composition is not impaired. For example, in the case where the structure to be inspected is constructed of a material which rusts easily such as iron, there may be added a rust preventive agent or the like.

As examples of the structure to which the present invention is applied, mention may be made of metal structures which are apt to be cracked due to metal fatigue such as ships, bridges, vehicles, aircraft and machine tools. However, as described for example in Japanese Patent No. 3329029, the present invention is applicable also to concrete structures by suitably selecting the diameter of the microcapsules with the visualizing liquid sealed therein. Likewise, the present invention is further applicable to various reinforced plastic structures.

EFFECT OF THE INVENTION

In the present invention, the second coating layer having a transparent and flexible outermost layer is laminated to the surface of the first coating layer having dispersed therein microcapsules containing the visualizing liquid, therefore, even if a crack is developed in the surface of a structure to be coated (a metal or concrete structure), the crack is not propagated to the outermost layer because the outermost layer is flexible, and hence the visualizing liquid flowing out from the capsules in the first coating layer does not flow out to the exterior of the coating layer, but stays within the coating layer and is protected by the transparent layer in the second coating layer. Consequently, the water resistance and waterproofness of the visualizing liquid are improved and the recognition of the cracked portion by the visualizing liquid is ensured over a long period.

EXAMPLES

Examples 1-5 and Comparative Example 1

<Production of Capsules>

Figure 1:
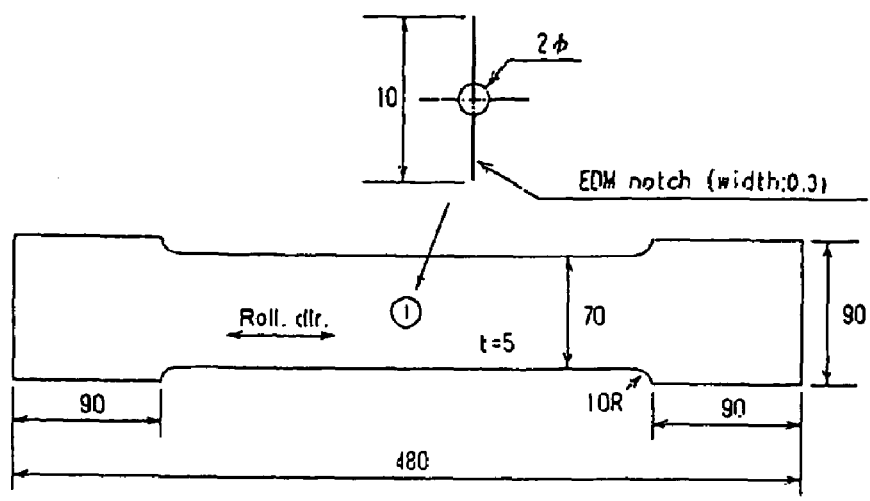
FIG. 1 is a plan view of a test piece used in the fatigue crack propagation test.

5500 parts by weight of oleic acid was added to 100 parts by weight of an azo dye (a product of Orient Kagaku Co.) and stirring was performed to prepare a visualizing liquid. (Azo dye:solvent=1:55) On the other hand, 450 parts by weight of gelatin (a product of Miyagi Kagaku Co., bloom strength: 320) was poured into 3600 parts by weight of water and was dissolved by stirring at 45° C. The visualizing liquid prepared above was poured into the resulting solution under stirring and was dispersed. Next, 450 parts by weight of gum arabic (a product of Wako Junyaku Co.) was poured into 3600 parts by weight of water, dissolved by stirring at 45° C. and filtered to remove insolubles. The resulting solution was poured into the dispersion prepared above. Then, 9000 parts by weight of water heated to 45° C. was added to the dispersion and then the pH of the dispersion was adjusted to 4.9 using 15% acetic acid. After the dispersion was cooled to 10° C., 200 parts by weight of a 25% glutaraldehyde solution (a product of Wako Junyaku Co.) was added thereto and stirring was performed at room temperature for about 8 hours to afford a microcapsule slurry. The slurry was then filtered and dried to afford microcapsules having an average diameter of about 115 μm.

<Coating Material>

400 parts by weight of a main agent/curing agent mixed, two-component coating material (EPICON T-500, a white coating material, a product of Chugoku Marine Paints Co.) was mixed with 100 parts by weight of the dried microcapsules.

The main agent and the curing agent were added in amounts of 340 parts by weight and 60 parts by weight, respectively, and were mixed together in advance (a coating material for the first coating layer, hereinafter referred to as the "microcapsule-containing epoxy coating material).

Example 1

<Preparing Test Piece for Evaluation Test>

The microcapsule-incorporated coating material prepared above was applied, using a brush, to a flat plate-like test piece (see FIG. 1) made of aluminum-magnesium alloy (JIS-A5083P-O) and was cured to form a first coating layer. Next, a two-component epoxy coating material (EPICON T-500, a white coating material, a product of Chugoku Marine Paints Co.) not containing the microcapsules was applied over the first coating material with use of a brush and was cured (an intermediate layer in a second coating layer). The thickness of the coating after drying was 100-150 μm (the total of both first coating layer and the intermediate layer in the second coating layer). Further, as a transparent outermost coating layer (a transparent layer in the second coating layer), an isobutylene rubber coating material (TB1171, a product of Three Bond Co.) was applied using a brush and was dried to solidify. The thickness of the coating after solidifying was 30-100 μm (only the transparent layer).

Example 2

A test piece was prepared in the same way as in Example 1 except that the intermediate layer in the second coating layer was not formed.

Example 3

A test piece was prepared in the same way as in Example 1 except that a styrene-butylene rubber coating material (TB2903B, a product of Three Bond Co.) was used as the outermost coating layer (the transparent layer in the second coating layer).

Example 4

A test piece was prepared in the same way as in Example 1 except that the intermediate layer in the second coating layer was not formed and that a styrene-butylene rubber coating material (TB2903B, a product of Three Bond Co.) was used as the outermost coating layer (the transparent layer in the second coating layer).

Example 5

<Production of Capsules>

5500 parts by weight of oleic acid was added to 100 parts by weight of a nigrosine compound (Solvent Black 7, a product of Chuo Gosei Kagaku Co.) and stirring was performed to prepare a visualizing liquid. (Nigrosine compound:solvent=1:55) On the other hand, 450 parts by weight of gelatin (a product of Miyagi Kagaku Co., bloom strength: 320) was poured into 3600 parts by weight of water and was dissolved by stirring at 45° C. The visualizing liquid prepared above was poured into the resulting solution under stirring and was dispersed. Next, 450 parts by weight of gum arabic (a product of Wako Junyaku Co.) was poured into 3600 parts by weight of water, dissolved by stirring at 45° C. and filtered to remove insolubles. The resulting solution was then poured into the dispersion prepared above. Subsequently, 9000 parts by weight of water heated to 45° C.

was added to the dispersion. Thereafter, the pH of the dispersion was adjusted to 4.9 using 15% acetic acid. The dispersion was cooled to 10° C., thereafter, 200 parts by weight of a h25% glutaraldehyde solution (a product of Wako Junyaku Co.) was added and stirring was performed at room temperature for about 8 hours to afford a microcapsule slurry. The slurry was filtered and dried to afford microcapsules having an average diameter of about 115 μm. A test piece was prepared in the same way as in Example 1 except that the microcapsules just prepared were used.

Comparative Example 1

A test piece was prepared in the same way as in Example 1 except that a transparent, reactive urethane coating material (Three Longie A-850, a product of Three Bond Co.) was used as the outermost coating layer.

<Evaluation Test—Fatigue Crack Propagation Test>

The test piece just prepared above, which has the dimensions (mm) shown in FIG. 1, was immersed in 3% artificial sea water (AQUAMARINE, a product of Yashima Yakuhin Co.) and in this state was loaded onto an electrohydraulic servo type fatigue tester (Shimadzu Servopulser, dynamic capacity: 10 tonf) and a fatigue crack propagation test was conducted under a complete pulsating repeated tensile load of frequency 4 Hz (load 0-1.6 tonf). The test was continued until growth of a crack to a length of about 20 mm after occurrence of the crack in the test piece (the number of times of repetition was about 200,000 to 450,000). Then, the appearance of the tested portion was observed visually, the results of which are shown in Table 1.

<Physical Property Test 1 of Outermost Coating Layer—Elongation Test Method>

<Production of Test Piece>

Figure 2:
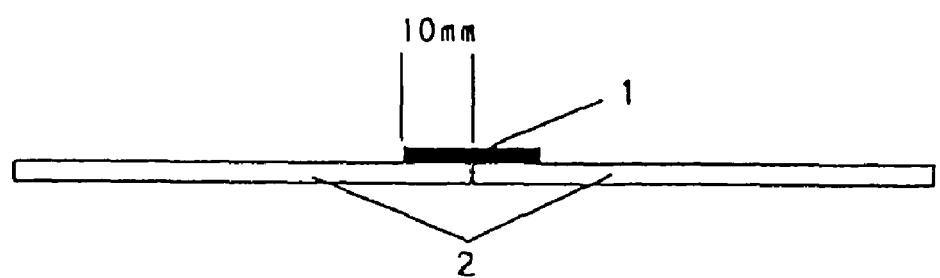
FIG. 2 is a side view of a test pieces used in the physical property test.

As shown in FIG. 2, two aluminum sheets (test pieces 2) (0.3×25×100 mm) were arranged side by side and each of the coating materials forming outermost coating layers and the two-component epoxy coating material were applied to the aluminum sheets with a brush and dried to afford coating layers 1. The film thickness after drying of each of the coating materials forming outermost coating layers was about 150 μm. After drying at room temperature for about 7 days, the test pieces were each pulled by a tension tester and the amount of elongation until rupture of the coating was measured. Further, an elongation quantity ratio was calculated by the following equation:

Elongation quantity ratio=(amount of elongation of each coating material forming the outermost coating layer)÷(amount of elongation of the two-component epoxy coating material)

The results obtained are also shown in Table 1.

<Physical Property Test 2—Adhesive Strength Test Method>

<Production of Test Piece>

The two-component epoxy coating material with a main agent and a curing agent mixed therein at a predetermined mixing ratio was applied onto two aluminum (JIS A1040P) sheets (100×25×2 mm) and then dried. The coating materials forming outermost layers were each applied to one of the aluminum sheets with a brush and, immediately thereafter, the thus-coated one sheet was affixed to the other sheet to afford test pieces. The test pieces were then tested in accordance with JIS K6850 Tensile Shear Adhesive Strength Test Method.

TABLE 1

| | Outermost Coating Layer/Presence or Absence of Intermediate Layer | Fatique Crack Propagation Test | | Physical Properties of Outermost Coating Layer | | |
|---|---|---|---|---|---|---|
| | | | | Elongation | | |
| | | Appearance before Test | State of Color Development | Amount of Elongation (mm) | Elongation Quality Ratio | Shear Strength (MPa) |
| Example 1 | TB1117/Present | Good | ◉ | 55 | 68.8 | 1.0 |
| Example 2 | TB1117/Absent | Somewhat uneven | ○ | — | — | — |
| Example 3 | TB2903/Present | Good | ◉ | 14 | 17.5 | 0.06 |
| Example 4 | TB2903/Absent | Somewhat uneven | ○ | — | — | — |
| Example 5 | TB1171/Present | Good | ◉ | 60 | 75 | 1.21 |
| Comparative Example 1 | Three Longie A-850/Present | Good | x | 3.7 | 4.6 | 2.7 |
| Microcapsule-containing epoxy coating material | | — | — | 0.8 | — | — |

◉: Extremely good
○: Good
x: Poor (the visualizing liquid flowed out and was lost)
—: unmeasured or immeasurable From the results obtained in Examples 1 to 5 it is seen that even if microcapsules are ruptured by a crack developed in the base material and the visualizing liquid flows out, the transparent outermost coating layer expands following the crack and causes the flowing-out visualizing liquid to stay within the coating layer, thus permitting the use of the coating in water or sea water or application thereof to a portion exposed to rain water. Besides, fading of the visualizing liquid with the lapse of time can be controlled. Moreover, in the case where a colored intermediate coating layer is provided as a second coating layer, a visual appearance can be improved because the microcapsules contained in the first coating layer are shielded; besides, by suitably combining the color of the visualizing liquid and that of the intermediate layer, it is possible to more emphasize the development of color and improve the visibility.

It is preferable that the elongation of the transparent outermost coating layer be usually not less than 5 mm (more preferably not less than 10 mm) although it depends on type of resin compositions used in the first and second coating layers (including an intermediate layer(s)). It is also seen that the adhesive strength between the transparent coating layer and the underlying layer is preferably relatively low (not higher than 2 MPa).

Examples 6-10 and Reference Examples 1-7

Example 6

5500 parts by weight of oleic acid was added to 100 parts by weight of a nigrosine compound (Solvent Black 7, a product of Chuo Gosei Kagaku Co.) and stirring was performed to prepare a visualizing liquid. (Nigrosine compound:solvent=1:55) On the other hand, 450 parts by weight of gelatin (a product of Miyagi Kagaku Co., bloom strength: 320) was poured into 3600 parts by weight of water and was dissolved by stirring at 45° C. The visualizing liquid prepared above was poured into the resulting solution under stirring and was dispersed. Next, 450 parts by weight of gum arabic (a product of Wako Junyaku Co.) was poured into 3600 parts by weight of water, dissolved by stirring at 45° C. and filtered to remove insolubles. The resulting solution was then poured into the dispersion prepared above. Subsequently, 900 parts by weight of water heated to 45° C. was added to the dispersion. Thereafter, the pH of the dispersion was adjusted to 4.9 using 15% acetic acid. The dispersion was cooled to 10° C., then 200 parts by weight of a 25% glutaraldehyde solution (a product of Wako Junyaku Co.) was added, followed by stirring at room temperature for about 8 hours, to afford a microcapsule slurry. The slurry was then filtered and dried, affording microcapsules having an average diameter of about 115 μm. Then, 400 parts by weight of a main agent/curing agent mixed, two-component epoxy coating material (EPICON T-500, a white coating material, a product of Chugoku Toryo Co.) was mixed with 100 parts by weight of the dried microcapsules. The main agent and the curing agent were added in amounts of 340 parts by weight and 60 parts by weight, respectively, and mixed together in advance. The mixed coating material was applied to an aluminum sheet (A11040P: 1×60×100 mm) using a brush to afford a test piece. The thickness of the coating after drying was 200 to 350 μm.

Example 7

A test piece was prepared in the same way as in Example 6 except that the mixing ratio of the visualizing liquid was changed to 460 parts by weight of oleic acid relative to 100 parts by weight of the nigrosine compound (Solvent Black 7, a product of Chuo Gosei Kagaku Co.). (Nigrosine compound:solvent =1:4.6)

Example 8

A test piece was prepared in the same way as in Example 6 except that the mixing ratio of the visualizing liquid was changed to 150 parts by weight of oleic acid relative to 410 parts by weight of the nigrosine compound (Solvent Black 7, a product of Chuo Gosei Kagaku Co.). (Nigrosine compound:solvent=1:0.37)

Example 9

A test piece was prepared in the same way as in Example 6 except that the mixing ratio of the visualizing liquid was changed to 260 parts by weight of spindle oil relative to 100 parts by weight of the nigrosine compound (Solvent Black 7, a product of Chuo Gosei Kagaku Co.). (Nigrosine compound:solvent=1:4.6)

Example 10

A test piece was prepared in the same way as in Example 6 except that the mixing ratio of the visualizing liquid was changed to 549 parts by weight of oleic acid relative to 11 parts by weight of the nigrosine compound (Solvent Black 7, a product of Chuo Gosei Kagaku Co.). (Nigrosine compound:solvent=1:50)

Reference Example 1

A test piece was prepared in the same way as in Example 6 except that the mixing ratio of the visualizing liquid was changed to 554 parts by weight relative to 6 parts by weight of the nigrosine compound (Solvent Black 7, a product of Chuo Gosei Kagaku Co.). (Nigrosine compound:solvent=1:91)

Reference Example 2

A test piece was prepared in the same way as in Example 6 except that the mixing ratio of the visualizing liquid was changed to 110 parts by weight of oleic acid relative to 450 parts by weight of the nigrosine compound (Solvent Black 7, a product of Chuo Gosei Kagaku Co.). (Nigrosine compound:solvent=1:0.24)

Reference Example 3

A test piece was prepared in the same way as in Example 6 except that as the visualizing liquid there was used a visualizing liquid prepared by mixing 110 parts by weight of an anthraquinone compound (1-amino-4-hydroxy-2-(4-n-nonylphenoxy)anthraquinone, a red dye, a product of Orient Kagaku Co.) and 450 parts by weight of mineral oil.

Reference Example 4

A test piece was prepared in the same way as in Example 6 except that the mixing ratio of the visualizing liquid was changed to 550.8 parts by weight of oleic acid relative to 9.2 parts by weight of the nigrosine compound (Solvent Black 7, a product of Chuo Gosei Kagaku Co.). (Nigrosine compound:solvent=1:60)

Reference Example 5

A test piece was prepared in the same way as in Example 6 except that as the visualizing liquid there was used a visualizing liquid prepared by mixing 110 parts by weight of an anthraquinone compound (OIL BLUE 5502, a blue dye, a product of Arimoto Kagaku Kogyo Co.), 225 parts by weight of toluene and 225 parts by weight of mineral oil.

Reference Example 6

A test piece was prepared in the same way as in Example 6 except that as the visualizing liquid there was used a visualizing liquid prepared by mixing 55 parts by weight of an anthraquinone compound (OIL BLUE 5502, a blue dye, a product of Arimoto Kagaku Kogyo Co.), 55 parts by weight of an azo compound (OIL YELLOW 5001, a product of Arimoto Kagaku Kogyo Co.), 225 parts by weight of toluene and 225 parts by weight of mineral oil.

Reference Example 7

A test piece was prepared in the same way as in Example 6 except that as the visualizing liquid there was used a visualizing liquid prepared by mixing 110 parts by weight of an azo compound (SOC-1-0092, an orange dye, a product of Orient Kagaku Co.) and 450 parts by weight of mineral oil.

<Test Method 1>

A part of the coating surface of each of the above test pieces was slit to a width of 1 mm or less and a length of about 5 cm by means of a cutter. The microcapsules present in the slit were ruptured and developed color.

The test piece was then placed into a weather meter and the state thereof after the lapse of 1000 hours was observed in the following manner.

The test piece was placed about 1.5 m under a daylight white fluorescent lamp (40 W×2) and was observed at a distance of about 1 m and at about 45° above the test piece. The results obtained are shown in Table 2.

TABLE 2

|  | Example |  |  |  |  | Reference Example |  |  |  |  |  |  |
| --- | --- | --- | --- | --- | --- | --- | --- | --- | --- | --- | --- | --- |
|  | 6 | 7 | 8 | 9 | 10 | 1 | 2 | 3 | 4 | 5 | 6 | 7 |
| Test Results | Δ | ⊚ | ○ | ⊚ | ○ | x | x | x | x | x | x | x |

⊚: Color can be identified easily.
○: Color can be identified.
Δ: A little difficult to identify color.
x: Impossible to identify color (fading).

Example 11

The aluminum sheet (A1040P: 1×60×100 mm) used in Example 6 was processed so as to be easily bent in half for example by slitting the central portion of the aluminum plate. Then, the microcapsule-containing epoxy resin coating material prepared in Example 6 was applied to the slit-free side of the aluminum sheet with use of a brush so as to give a coating thickness after drying of 200 to 350 μm and then dried. In this way there were produced ten test pieces.

The test pieces were bent about 90° along the respective slit portions so that one group of five were placed with their coated surfaces inside and the other group of five were placed with their coated surfaces outside. As a result, in all of the test pieces, linear cracks were developed in the coating surfaces and in the vicinity of the bent portions and the development of color caused by flowing-out of the nigrosine compound with rupture of the microcapsules could be confirmed.

As is seen also from the results obtained in Examples 6 to 10, the use of the nigrosine compound as the dye contained in the capsules results in a remarkable improvement of weathering resistance in comparison with other dyes and permits a visual confirmation of color development over a long period.

The invention claimed is:

1. A coating for the inspection of a crack in a structure wherein a first coating layer having dispersed therein microcapsules with a visualizing liquid sealed therein is formed on the surface of the structure and when a crack is developed in said structure and propagated to said coating layer, the microcapsules dispersed in said coating layer are ruptured and said visualizing liquid flows out from the ruptured microcapsules and reaches the surface of the coating layer along the crack in the coating layer, thereby making it possible to detect the occurrence of the crack in said structure, wherein at least one second coating layer not containing the microcapsules is formed over said first coating layer with the microcapsules dispersed therein, and said second coating layer being transparent and having an outermost layer capable of elongating at least seventeen times the amount of elongation of any other coating layer in said structure.

2. A coating for the inspection of a crack in a structure according to claim 1, wherein said visualizing liquid sealed in said microcapsules contains as principal components a nigrosine compound and a solvent in a weight ratio of the nigrosine compound to the solvent in the range of 1:55 to 1:0.37.

3. A coating for the inspecting of a crack in a structure according to claim 1, wherein an adhesive strength under shear between the outermost layer in said second coating layer and the immediately underlying coating layer is not higher than 1 MPa.

4. A coating for the inspection of a crack in a structure according to claim 1, wherein said second coating layer comprises an opaquely colored intermediate layer and a transparent outermost layer.

5. A coating for the inspection of a crack in a structure according to claim 1, wherein said structure is a metallic structure.

6. A coating for the inspection of a crack in a structure according to claim 2, wherein said second coating layer comprises an opaquely colored intermediate layer and a transparent outermost layer.

7. A coating for the inspection of a crack in a structure according to claim 3, wherein said second coating layer comprises an opaquely colored intermediate layer and a transparent outermost layer.

8. A coating for the inspection of a crack in a structure according to claim 7, wherein said structure is a metallic structure.

9. A coating for the inspection of a crack in a structure according to claim 1, wherein said structure is a metallic structure.

10. A coating for the inspection of a crack in a structure according to claim 2, wherein said structure is a metallic structure.

11. A coating for the inspection of a crack in a structure according to claim 3, wherein said structure is a metallic structure.

12. A coating for the inspection of a crack in a structure according to claim 1, wherein said first coating layer comprises an epoxy, urethane, acryl, nitrocellulose, silicone or modified silicone resin.

13. A coating for the inspection of a crack in a structure according to claim 1, wherein the second coating layer comprises a solvent-diluted rubbery coating material or a fluid composition containing at least one resin selected from the group consisting of epoxy resin, urethane resin, acrylic resin, silicon resin, or copolymer rubber.

14. A coating for the inspection of a crack in a structure according to claim 13 comprising the solvent-diluted rubbery coating material, wherein the solvent-diluted rubbery coating material is polyisobutylene rubber or styrene-butylene copolymer rubber.

15. A coating for the inspection of a crack in a structure wherein a coating layer having dispersed therein microcapsules with a visualizing liquid sealed therein is formed on the surface of the structure and when a crack is developed in said structure and propagated to said coating layer, the microcapsules dispersed in said coating layer are ruptured and said visualizing liquid flows out from the ruptured microcapsules and reaches the surface of the coating layer along the crack in the coating layer, thereby making it possible to detect the occurrence of the crack in said structure, wherein said visualizing liquid sealed in said microcapsules contains as principal components a nigrosine compound and a solvent in a weight ratio of the nigrosine compound to the solvent in the range 1:55 to 1:0.37.

16. A coating for the inspection of a crack in a structure wherein a first coating layer having dispersed therein microcapsules with a visualizing liquid sealed therein is formed on the surface of the structure and when a crack is developed in said structure and propagated to said coating layer, the microcapsules dispersed in said coating layer are ruptured and said visualizing liquid flows out from the ruptured microcapsules and reaches the surface of the coating layer along the crack in the coating layer, thereby making it possible to detect the occurrence of the crack in said structure, wherein at least one second coating layer not containing the microcapsules is formed over said first coating layer with the microcapsules dispersed therein, and said second coating layer being transparent and having an outermost layer flexible enough to be prevented from being cracked even upon cracking in the first coating layer, said first coating layer comprising an epoxy resin.

17. A coating for the inspection of a crack in a structure wherein a coating layer having dispersed therein microcapsules with a visualizing liquid sealed therein is formed on the surface of the structure and when a crack is developed in said structure and propagated to said coating layer, the microcapsules dispersed in said coating layer are ruptured and side visualizing liquid flows out from the ruptured microcapsules and reaches the surface of the coating layer along the crack in the coating layer, thereby making it possible to detect the occurrence of the crack in said structure, wherein at least one second coating layer not containing the microcapsules is formed over said first coating layer with the microcapsules dispersed therein, and said second coating layer comprises polyisobutylene rubber or styrene-butylene copolymer rubber is transparent and has an outermost layer flexible enough to be prevented from being cracked even upon cracking in the first coating layer.

18. A coating for the inspection of a crack in a structure wherein a first coating layer having dispersed therein microcapsules with a visualizing liquid sealed therein is formed on the surface of the structure and when a crack is developed in said structure and propagated to said coating layer, the microcapsules dispersed in said coating layer are ruptured and said visualizing liquid flows out from the ruptured microcapsules and reaches the surface of the coating layer along the crack in the coating layer, thereby making it possible to detect the occurrence of the crack in said structure, wherein at least one second coating layer not containing the microcapsules is formed over said first coating layer with the microcapsules dispersed therein, and said second coating layer being transparent and having an outermost layer flexible enough to be prevented from being cracked even upon cracking in the first coating layer wherein said second coating layer comprises an opaquely colored intermediate layer and a transparent outermost layer and said intermediate layer comprises at least one resin selected from the group consisting of an epoxy resin, urethane resin, acrylic resin, silicone resin and modified silicone resin.

\* \* \* \* \*